(12) United States Patent
Yuasa et al.

(10) Patent No.: US 12,161,297 B2
(45) Date of Patent: Dec. 10, 2024

(54) TREATMENT DEVICE

(71) Applicant: OLYMPUS CORPORATION, Tokyo (JP)

(72) Inventors: Masaru Yuasa, Allentown, PA (US); Yoshisane Nakamura, Allentown, PA (US); Lon B. Miller, Maple Grove, MN (US); Yung N. Nguyen, Bloomington, MN (US); Vincen V. Vang, Brooklyn Center, MN (US); Yohei Yoshida, Allentown, PA (US)

(73) Assignee: OLYMPUS CORPORATION, Tokyo (JP)

( * ) Notice: Subject to any disclaimer, the term of this patent is extended or adjusted under 35 U.S.C. 154(b) by 693 days.

(21) Appl. No.: 17/490,536

(22) Filed: Sep. 30, 2021

(65) Prior Publication Data
US 2022/0015615 A1    Jan. 20, 2022

Related U.S. Application Data

(63) Continuation of application No. PCT/IB2020/000224, filed on Mar. 23, 2020, which
(Continued)

(51) Int. Cl.
*A61B 1/012* (2006.01)
*A61B 1/00* (2006.01)
(Continued)

(52) U.S. Cl.
CPC ........ *A61B 1/0125* (2013.01); *A61B 1/00087* (2013.01); *A61B 1/0055* (2013.01);
(Continued)

(58) Field of Classification Search
CPC ... A61B 1/0125; A61B 1/0087; A61B 1/0055; A61B 1/01; A61B 1/018; A61B 17/221;
(Continued)

(56) References Cited

U.S. PATENT DOCUMENTS 7,387,632 B2    6/2008    Ouchi
7,951,073 B2    5/2011    Freed
(Continued)

FOREIGN PATENT DOCUMENTS

JP    2007-289701 A    11/2007
JP    2009-61250 A    3/2009
(Continued)

OTHER PUBLICATIONS

Oct. 25, 2022 Office Action issued in Japanese Patent Application No. 2021-558963.
(Continued)

*Primary Examiner* — Linda C Dvorak
*Assistant Examiner* — Abigail Bock
(74) *Attorney, Agent, or Firm* — Oliff PLC

(57) ABSTRACT

A treatment device includes a flexible sheath; a wire configured to be inserted into the sheath; a first treatment member disposed at distal side from the wire; a second treatment member disposed at a distal side from the first treatment member; and a protection member configured to cover the second treatment member when the first treatment member projects from a distal end of the sheath.

20 Claims, 8 Drawing Sheets

Related U.S. Application Data is a continuation of application No. 16/374,078, filed on Apr. 3, 2019, now Pat. No. 10,980,402.

(51) Int. Cl.

| | | |
|---|---|---|
| *A61B 1/005* | (2006.01) | |
| *A61B 1/01* | (2006.01) | |
| *A61B 1/018* | (2006.01) | |
| *A61B 17/221* | (2006.01) | |
| *A61B 17/32* | (2006.01) | |
| *A61B 18/14* | (2006.01) | |
| *A61B 18/00* | (2006.01) | |

(52) U.S. Cl.
CPC ............... *A61B 1/01* (2013.01); *A61B 1/018* (2013.01); *A61B 17/221* (2013.01); *A61B 17/32* (2013.01); *A61B 18/1492* (2013.01); *A61B 2018/00494* (2013.01); *A61B 2018/00601* (2013.01); *A61B 2018/141* (2013.01); *A61B 2018/1412* (2013.01); *A61B 2018/1417* (2013.01); *A61B 2018/1475* (2013.01)

(58) Field of Classification Search
CPC ............... A61B 17/32; A61B 18/1492; A61B 2018/00494; A61B 2018/00601; A61B 2018/141; A61B 2018/1412; A61B 2018/1417; A61B 2018/1475

See application file for complete search history.

(56) References Cited

U.S. PATENT DOCUMENTS

| | | |
|---|---|---|
| 9,486,229 B2 | 11/2016 | Aufer |
| 2005/0131424 A1 | 6/2005 | Ouchi |
| 2016/0175042 A1 | 6/2016 | McLawhorn |

FOREIGN PATENT DOCUMENTS

| | | |
|---|---|---|
| JP | 2009-125344 A | 6/2009 |
| JP | 2010-131100 A | 6/2010 |
| JP | 2013-158429 A | 8/2013 |
| WO | 2017/122546 A1 | 7/2017 |

OTHER PUBLICATIONS

Dec. 30, 2020 Notice of Allowance Issued in U.S. Appl. No. 16/374,078.

Jul. 31, 2020 Search Report issued in International Patent Application No. PCT/IB2020/000224.

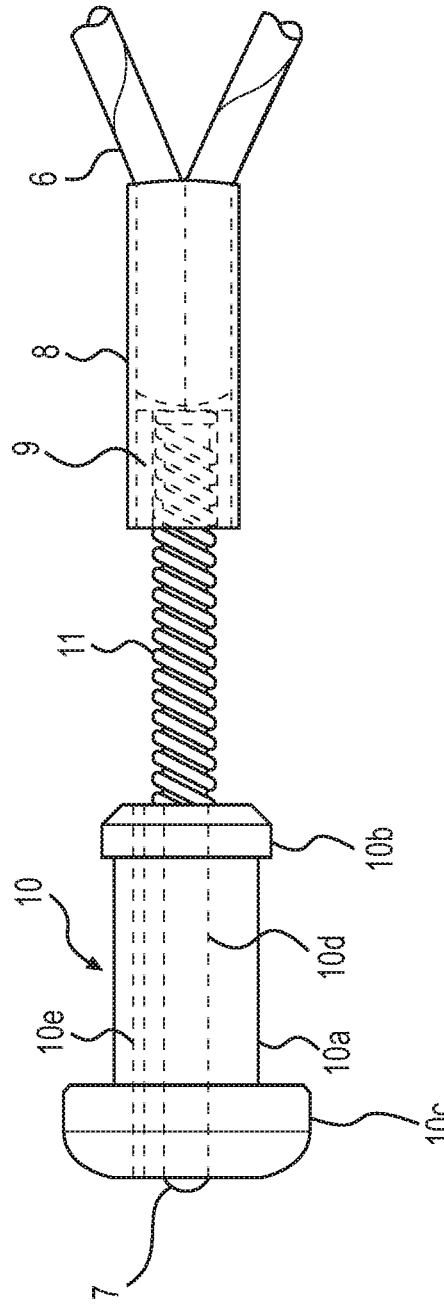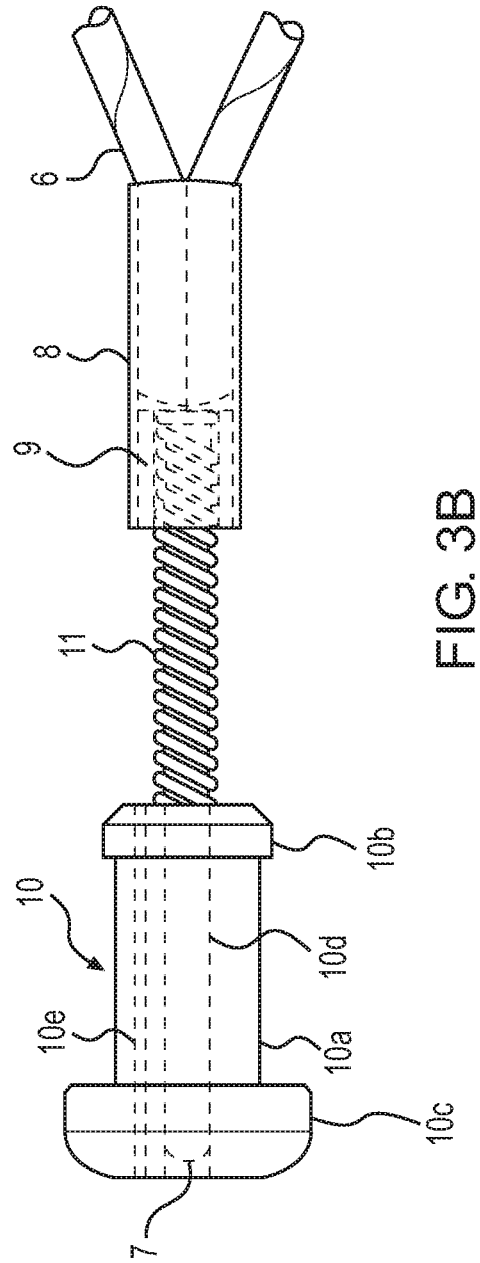
FIG. 3A
FIG. 3B

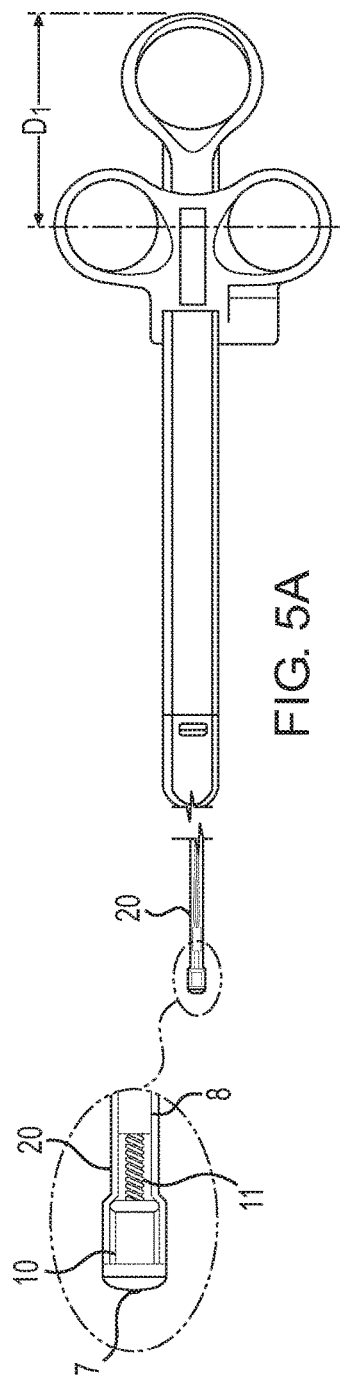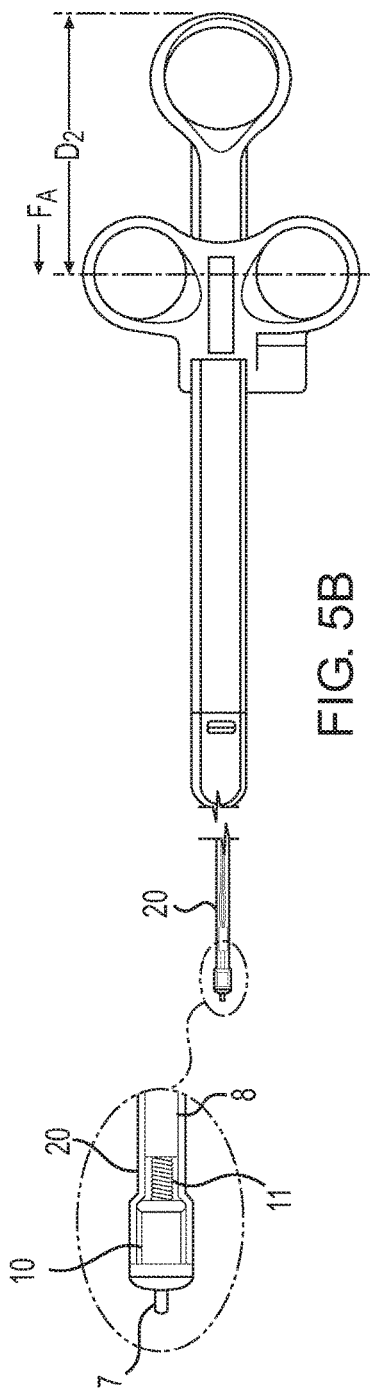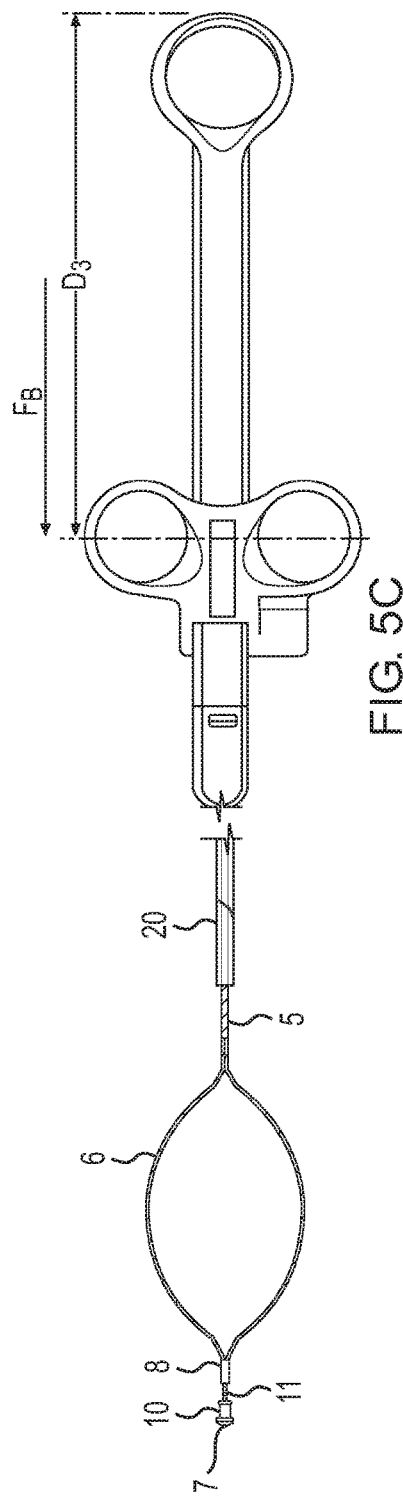
FIG. 5A
FIG. 5B
FIG. 5C

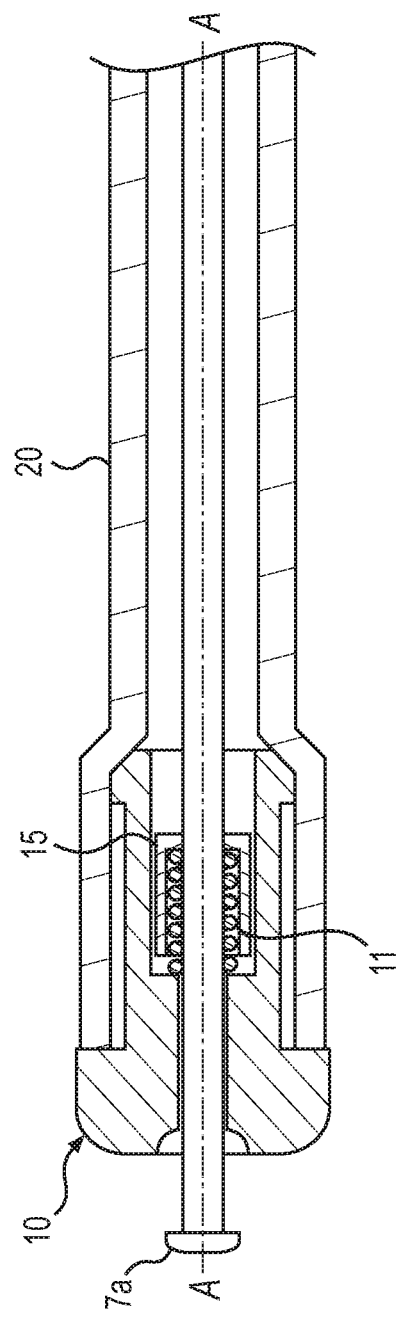
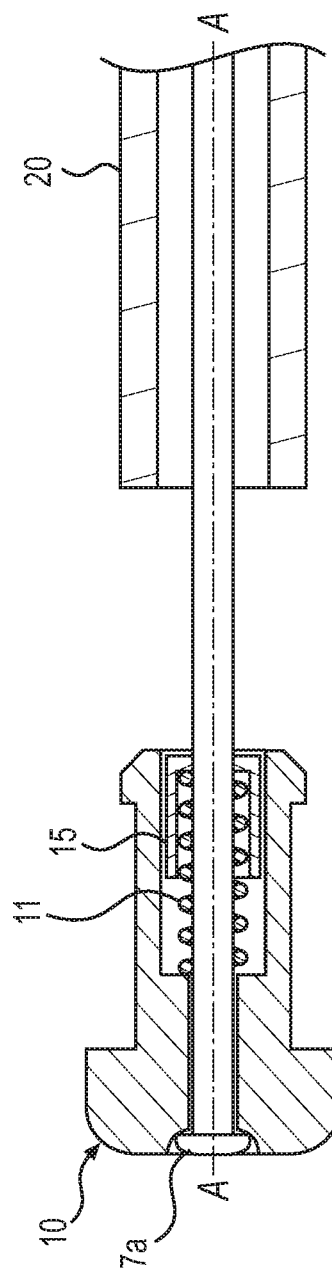

TREATMENT DEVICE

This application is a continuation application based on International Patent Application No. PCT/IB2020/000224 filed on Mar. 23, 2020, which is itself a continuation of U.S. patent application Ser. No. 16/374,078, filed on Apr. 3, 2019, the contents of which are incorporated herein by reference.

BACKGROUND

Colon cancer is the second biggest cancer killer in the United States, claiming nearly 50,000 lives a year. Colon cancer usually starts from a benign colon polyp (an adenoma), a small clump of cells that forms on the lining of the colon. About 15 to 25% of people have at least one colon polyp by age 50 (when screening for colorectal cancer typically starts), and up to half of the population will develop colon polyps in their lifetime.

Although most colon polyps are harmless, some can develop into colon cancer, which is often fatal when found in its later stages. It is estimated that about 5% of all adenomas would eventually develop into cancer if not removed. When detected, polyps should be removed in order to examine the tissue to determine whether the growths are cancerous, precancerous, or benign. This can prevent colon cancer.

Currently, the main endoscopic techniques that are available for the removal of colon polyps include endoscopic mucosal resection (EMR) and endoscopic submucosal dissection (ESD).

EMR is performed with a snare to capture the target tissue. Saline can optionally be injected into the submucosal space to elevate the lesion and facilitate its removal. An electrosurgical current is then passed through the snare in order to transect the tissue that has been grasped. If the lesion is larger than 15 to 20 mm, it typically has to be removed in a piecemeal fashion.

By contrast, ESD is performed by injecting fluid into the submucosa and creating an incision around the perimeter of the lesion, and then carefully dissecting the lesion from the deeper layers. Various specialized instruments (ESD knives) are used to dissect the tissue. Generally speaking, ESD is recommended for removing lesions that have a high likelihood of invading the superficial submucosa and for lesions that cannot be removed by EMR due to fibrosis in the submucosal space or post-EMR recurrences.

ESD allows en bloc resection (resection of a lesion as a whole mass) of any type of lesion regardless of size. Removing the entire lesion in a single piece allows for accurate histologic assessment and reduces the likelihood of recurrence (to less than 1%). However, ESD is technically more demanding than EMR and requires advanced endoscopy skills. Furthermore, ESD is a longer procedure associated with a higher perforation rate compared to EMR.

To overcome these difficulties with ESD, modified endoscopic procedures have been introduced, such as ESD with snaring and EMR with circumferential incision. These hybrid procedures involve initial incision around the tumor (circumferential incision) akin to the ESD procedure, followed by snaring the tumor using the EMR technique. Accordingly, there is a need for two types of instruments to complete the procedure: a cutting device (e.g., a knife) and a snare. The treatment instruments (e.g., knife and snare) must be interchanged with one another during the procedure, which complicates the endoscopic surgical operation and raises the possibility of contamination each time one of the instruments is changed out.

Accordingly, there is a need for a diathermic endotherapeutic device that allows for interchange between more than one instrument during a procedure without requiring complete removal of an instrument when that instrument is not in use. To avoid unintended trauma to the tissue, only one instrument should be exposed at any given time.

SUMMARY

The disclosed embodiments include a treatment device that includes a flexible sheath, a wire configured to be inserted into the sheath; a first treatment member disposed at distal side from the wire; a second treatment member disposed at a distal side from the first treatment member; and a protection member configured to cover the second treatment member when the first treatment member projects from a distal end of the sheath.

Many modifications are possible without materially departing from the teachings of the detailed description. Accordingly, such modifications are intended to be included within the scope of the disclosure as defined in the claims.

BRIEF DESCRIPTION OF THE DRAWINGS

These and other aspects and features of the invention will become apparent to those of ordinary skill in the art upon review of the following description in conjunction with the accompanying figures.

FIG. 3A shows a detailed view of the distal end of the treatment device, and FIG. 3B shows a detailed view of the distal end of another treatment device of the disclosed embodiments.

FIGS. 5A-5C show three different modes of using the treatment device.

FIGS. 7A and 7B show first and second treatment modes of a "dual-knife" treatment device of the disclosed embodiments.

DETAILED DESCRIPTION OF EMBODIMENTS

The disclosed embodiments have been devised to address the above-mentioned problems. In particular, the disclosed embodiments include a treatment device that allows for interchanging between first and second treatment members during an endoscopic procedure without requiring that either treatment member be removed when that treatment member is not in use. To avoid unintended trauma to the tissue, the treatment device can alternate between different modes that determine which, if any, of the treatment members is exposed.

Various implementations are now described in detail in relation to the drawings. These exemplary implementations of the inventive principles are intended as illustrative only since numerous modifications and variations will be apparent to those skilled in the art.

The disclosed embodiments include a diathermic endotherapeutic system, as described below.

Figure 1:
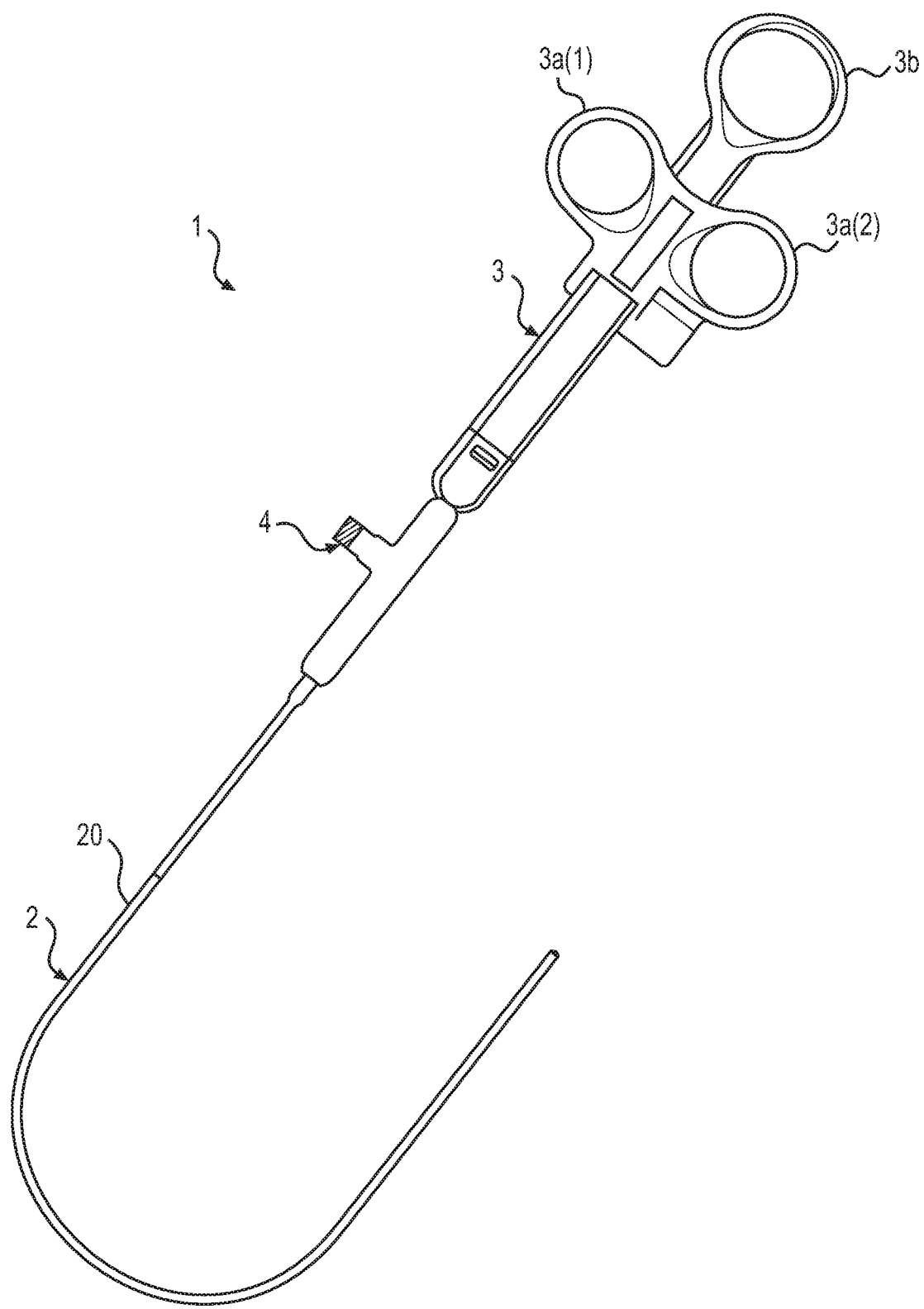
FIG. 1 shows a treatment device according to the disclosed embodiments.

A diathermic endotherapeutic system of the disclosed embodiments comprises a treatment device (a diathermic endotherapeutic device) and peripheral devices, such as a power source or pump. As shown in FIG. 1, the treatment device 1 includes an insertion portion 2 configured to be inserted into a body cavity via an endoscope (not shown). The insertion portion 2 includes a flexible sheath 20 that is an elongated tubular member approximately 200 cm long. The inner diameter of the flexible sheath 20 is approximately constant throughout the length of the flexible sheath 20, except that it may be smaller at the distal end of the flexible sheath 20.

The treatment device 1 includes a handle assembly 3 operatively (and optionally, removably) coupled to a proximal end of the insertion portion 2. The handle assembly 3 is configured to be held by an operator during an endoscopic procedure, and to switch the treatment device 1 between different modes. FIG. 1 shows the handle assembly 3 configured as a three-ringed structure for gripping by the treatment device 1 operator, although other configurations for the handle assembly 3 may be possible.

To hold the three-ringed handle assembly 3, the operator places the index finger and middle finger through a first lateral ring 3a(O) and second lateral ring 3a(2) (collectively referred to herein as the two lateral rings 3a), and the thumb through the proximal-most ring 3b. The two lateral rings 3a are slidably connected to the remainder of the handle assembly 3 and are operatively connected to a control wire 5 (wire) via a plug 12, which is shown in FIG. 2B.

The treatment device 1 also includes an accessory port 4 that allows coupling of the treatment device 1 to other instruments. For example, the accessory port 4 can be connected to a pump or syringe (not shown) in order to administer saline and/or other medicaments to the treatment site. When a fluid such as saline is administered, the fluid passes through the lumen of the flexible sheath 20 to the distal end of the flexible sheath 20, and is ejected from the distal end of the flexible sheath 20 while the flexible sheath 20 is positioned at the treatment site.

Figure 2A:
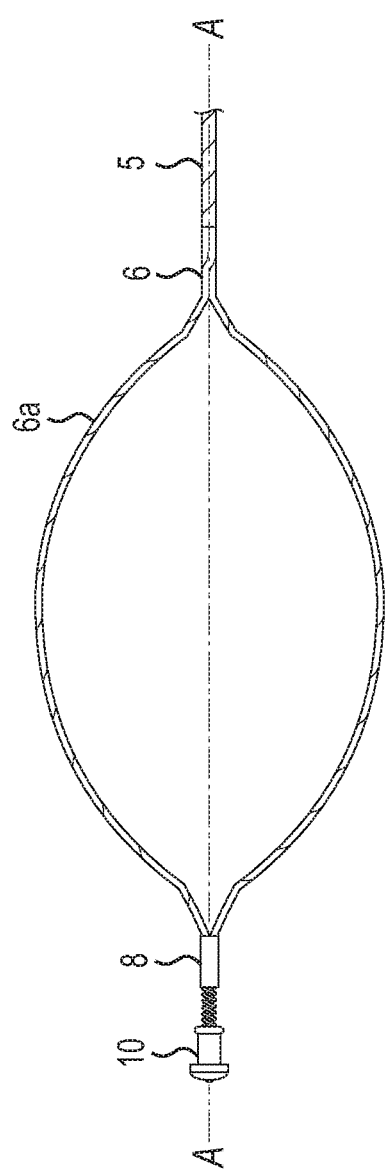
FIG. 2A shows a side view of a distal portion of the treatment device.
Figure 2B:
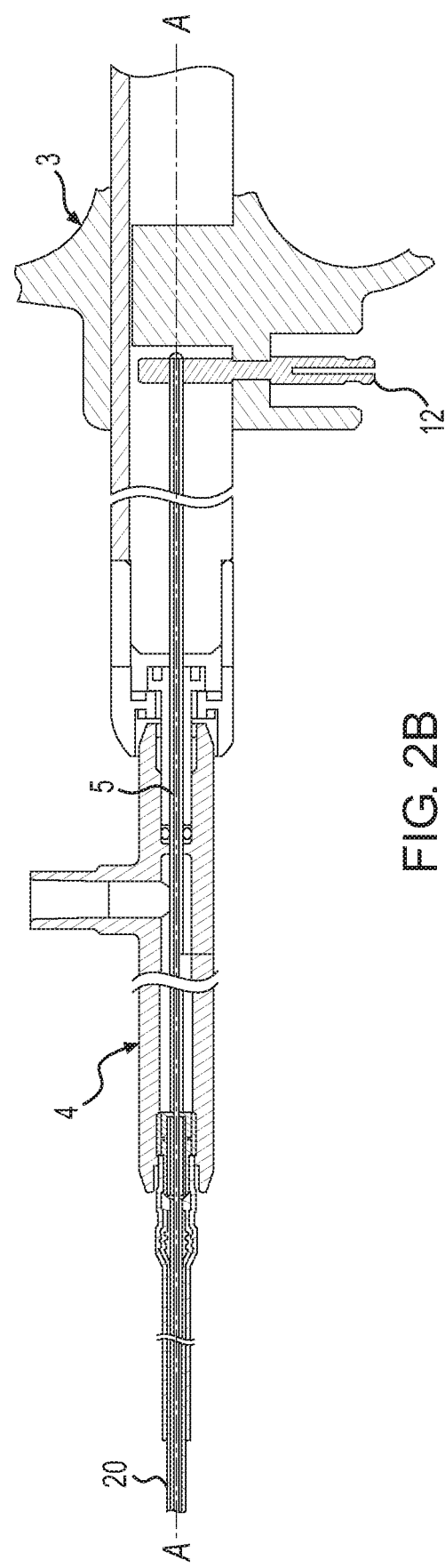
FIG. 2B shows a cross-sectional view of a proximal portion of the treatment device.

As shown in FIGS. 2A-2B, the control wire 5 is inserted into the flexible sheath 20 so as to move forward and backward (distally and proximally) in response to movement of the handle assembly 3, and a first treatment member is coupled to a distal end of the control wire 5. In the embodiment shown, the first treatment member is a snare 6.

The snare 6 includes a loop section 6a that expands by its own elasticity to form a loop. The snare 6 moves forward and backward in the axial direction of the flexible sheath 20 in response to movement of the control wire 5. When the control wire 5 is pushed forward (distally) in order to enter a snare mode, the loop section 6a of the snare 6 projects from the distal end of the flexible sheath 20 and expands by its own elasticity to form a loop. When the control wire 5 is pulled backward (proximally), the loop section 6a of the snare 6 is retracted into the flexible sheath 20 and is stored within the flexible sheath 20.

The insertion portion 2 further includes a second treatment member coupled to a distal end of the first treatment member. Throughout this disclosure, unless indicated otherwise, members can be directly coupled to each other via conventional means, such as brazing, soldering, welding, or clamping. Thus, the distal end of the first treatment member can be connected to the proximal end of the second treatment member through any of these means.

As shown in FIGS. 1-5C and 7A-8B, the second treatment member may be used for cutting. For example, the second treatment member may be a diathermic knife 7.

As shown in detail in FIGS. 3A-3B, the insertion portion 2 of the treatment device 1 includes a snare 6 as the first treatment member and a knife 7 as the second treatment member. The snare 6 and knife 7 are clamped together via a cylindrical connection tube 8, which stabilizes the junction between the treatment members. In order to further stabilize the knife 7 and keep the knife 7 centered, a spacer 9 may be included within the distal portion of the connection tube 8. As shown, the spacer 9 is positioned between the knife 7 and the inner circumference of the connection tube 8 in a radial direction (i.e., within the lumen of the connection tube 8). The proximal portion of the knife 7 extends through the spacer 9 and the connection tube 8. For example, approximately 1 mm of the knife 7 extends into the spacer 9 and connection tube 8.

The treatment device 1 further includes an insulating protection member 10, which controls how much of the second treatment member is exposed by covering portions of the second treatment member based on which mode of operation that the operator requires from the treatment device 1. Details of an exemplary protection member 10 according to the disclosed embodiments are set forth below.

The protection member 10 is a cylindrical member through which the second treatment member can project or retract. The protection member 10 includes an elongated tubular section 10a, and proximal and distal protruding portions 10b, 10c that respectively protrude from proximal and distal ends of the elongated tubular section 10a, forming a flange at each end of the elongated tubular section 10a. The elongated tubular section 10a and proximal and distal protruding portions 10b, 10c may together form a monolithic structure formed of a ceramic material (e.g., zirconia). A lumen 10d having a constant diameter extends from the proximal end of the protection member 10 to the distal end of the protection member 10, and permits passage of the second treatment member. The protection member 10 may also include an aperture 10e for passage of any fluid injected via the accessory port 4.

The distal protruding portion 10c of the protection member 10 may be tapered at its proximal and distal ends so that an outer diameter of the distal protruding portion 10c decreases in the axial direction from a center region of the distal protruding portion 10c toward the proximal and distal ends of the distal protruding portion 10c. The maximum outer diameter of the distal protruding portion 10c is approximately the same as the outer diameter of the flexible sheath 20. Accordingly, the distal protruding portion 10c remains outside the flexible sheath 20 and forms a distal tip of the insertion portion 2.

The proximal protruding portion 10b of the protection member 10 may be tapered at its proximal end so that an outer diameter of the proximal protruding portion 10b decreases in the axial direction from a center region of the proximal protruding portion 10b toward the distal end of the proximal protruding portion 10b. The maximum outer diameter of the proximal protruding portion 10b is smaller than the maximum outer diameter of the distal protruding portion 10c of the protection member 10, but larger than an inner diameter of the distal end of the flexible sheath 20. Accordingly, the proximal protruding portion 10b can be removably press fit into the distal end of the flexible sheath 20 so that the flexible sheath 20 stretches around the proximal protruding portion 10b. As used herein, the term "press fit" refers to an interference fit in which two parts are fastened by friction after the parts are pushed together, rather than by any other means of fastening.

Figure 4A:
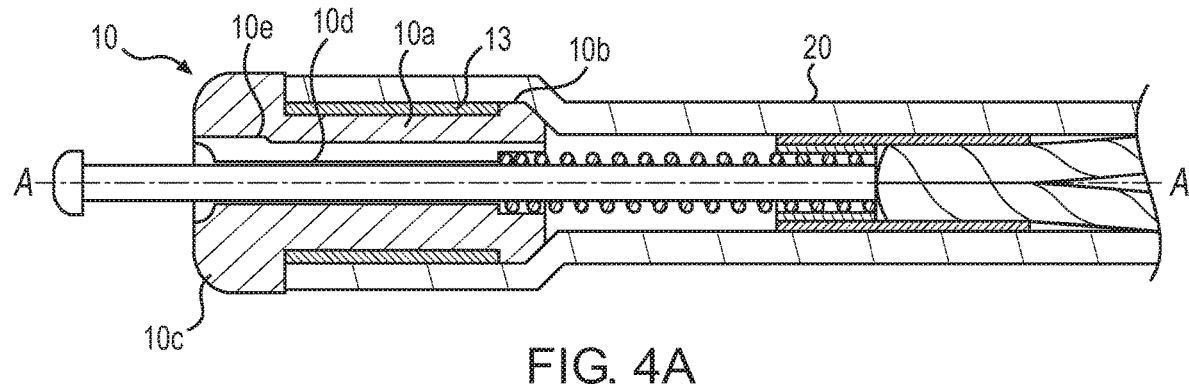
FIGS. 4A-4C show different detailed views of the distal end of other treatment devices of the disclosed embodiments.

The protection member 10 can optionally include an elastic member 13 covering at least a portion of the elongated tubular section 10a, as shown in FIG. 4A. For example, the elastic member 13 may be a tubular member that covers an entire outer circumference of the elongated tubular section 10a. The outer diameter of the elastic member 13 may be approximately the same as the maximum outer diameter of the proximal protruding portion 10b. The elastic member 13 is formed of an elastic material that has a higher coefficient of friction than the material of the monolithic structure. For example, the elastic material may be rubber, silicone, a gel, or an adhesive, and the elastic member 13 may be in the form of a sponge or O-ring. Accordingly, the elastic member 13 increases the fastening strength between the protection member 10 and the flexible sheath 20 when the protection member 10 and the flexible sheath 20 are press fit together.

Figure 4B:
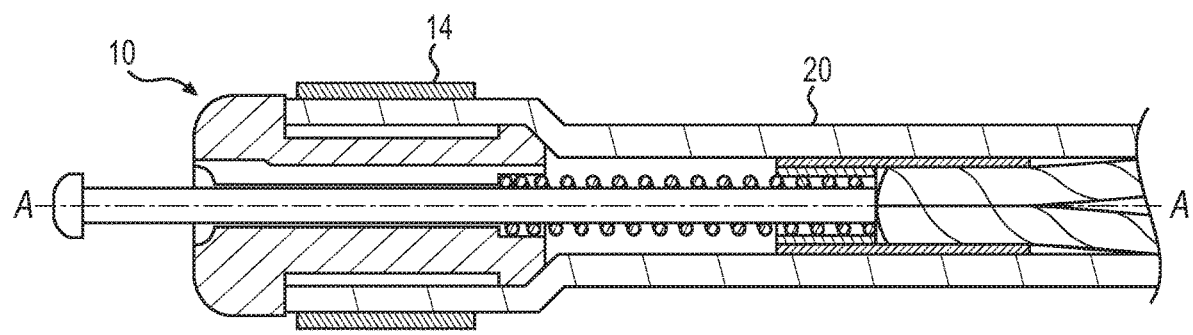

Alternatively or additionally, a distal portion of the flexible sheath 20 may be covered with a metal member 14, as shown in FIG. 4B. The metal member 14 is a metal tube or ring, and is stiffer than the flexible sheath 20. Accordingly, the metal member prevents the distal portion of the flexible sheath from radially expanding when the protection member 10 is press fit into the flexible sheath 20, and thus increases the fastening strength.

Figure 4C:
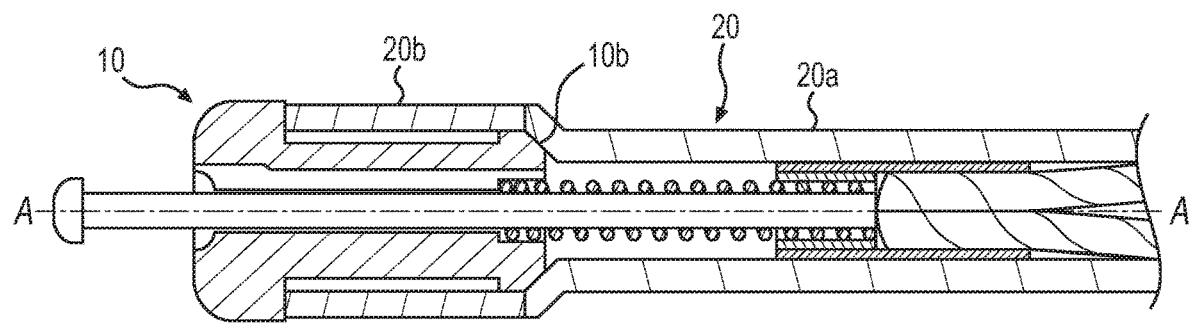

To further increase the fastening strength, a distal section 20b of the flexible sheath 20 may be stiffer than the remainder 20a of the flexible sheath, and may even be formed from a stiffer (different) material than the remainder of the flexible sheath 20, as shown in FIG. 4C. For example, the distal section 20b may be formed of a stiff plastic material, such as polyether ether ketone (PEEK), and the remainder 20a of the flexible sheath may be formed of a softer material, such as silicone, nylon, polyurethane, polyethylene terephthalate (PET), polytetrafluoroethylene (PTFE), polypropylene (PP), latex, etc. The distal section 20b may or may not extend past the proximal end of the protection member 10 in the proximal direction when the protection member 10 is press fit into the flexible sheath 20. In the example shown in FIG. 4C, the distal section 20b extends in the proximal direction to at least the proximal protruding portion 10b.

The proximal end of the protection member 10 is coupled to the first and/or second treatment member, at the junction between the treatment members, via an energization member that is configured to energize the protection member 10 in the distal direction so that the protection member 10 covers the second treatment member. The energization member can be a spring 11, for example.

In FIGS. 3A-3B, the spring 11, together with the knife 7, extends through the spacer 9 and connection tube 8 (which can function as a second insulating protection member) and is fixed to a distal end of the snare 6. For example, the spring 11 and snare 6 may be fixed to each other via brazing. The knife 7 extends through the length of the spring 11. Accordingly, when the snare 6 moves in the distal direction, the knife 7 and the proximal end of the spring 11 (which are each connected to the distal end of the snare 6) also move in the distal direction. Likewise, when the snare 6 moves in the proximal direction, the knife 7 and the proximal end of the spring 11 also move in the proximal direction.

The distal end of the spring 11 is coupled to the proximal end of the protection member 10 (for example, by brazing), but is not fixed to the second treatment member. When the proximal protruding portion 10b of the protection member 10 is press fit into the flexible sheath 20 and the snare 6 is moved in the distal direction, the knife 7 moves distally and the spring 11 compresses. Because the proximal protruding portion 10b of the protection member 10 is press fit into the flexible sheath 20, the protection member 10 will not detach from the flexible sheath 20 unless a predetermined amount of force is exerted on the snare 6 that is sufficient to compress the spring 11 beyond its maximum compression capacity. When the spring 11 can no longer be compressed, further distal movement of the snare 6 will eject the spring 11 and protection member 10 outside of the flexible sheath 20. In this way, the placement of the protection member 10 controls how much of the second treatment member is exposed at any given time.

For example, in a preparation mode discussed further below, the protection member 10 covers the distal portion of the second treatment member so that the second treatment member does not cause accidental mechanical or electrical trauma to surrounding tissue. The distal portion of the second treatment member can be fully housed within the protection member 10, or the treatment device 1 can be configured such that only a distal-most end of the second treatment member is exposed outside the distal end of the protection member 10 in the preparation mode. Even if a distal-most end of the second treatment member is exposed, however, the length of the exposed portion is sufficiently short such that the protection member 10 prevents the second treatment member from causing undesirable damage to any surrounding tissue.

For example, as shown in FIG. 5A, the distal portion of the knife 7 is covered by the protection member 10, which is housed within the flexible sheath 20. As shown, a distal-end surface of the knife 7 is exposed at the distal end of the protection member 10. Accordingly, the operator can mark tissue or stop bleeding (cauterize) by contacting the tissue with the activated distal-end surface of the knife 7. However, lateral surfaces of the knife 7 (the circumferential surface along the length of the knife 7) are effectively entirely covered by the protection member 10 and cannot come into contact with any surrounding tissue. As used herein, "effectively entirely covered" means that the relevant surfaces are covered to such a degree that the surfaces cannot contact and energize surrounding tissue when the device is in use. Thus, the length of the exposed portion of the knife 7 is sufficiently short such that contact between the distal-end surface of the knife 7 and the tissue will only cause discoloration of the tissue, and will not compromise the health of the tissue.

Alternatively, the distal portion of the knife 7 may be entirely covered by and housed within the protection member 10 such that even the distal-end surface of the knife 7 is positioned within the lumen 10d of the protection member 10 and is covered by the protection member 10.

In a first treatment mode, the protection member 10 is housed within the flexible sheath 20 and covers a medial portion of the second treatment member, and the distal portion of the second treatment member extends from the distal end of the protection member 10. For example, in FIG. 5B, the distal portion of the knife 7 (the second treatment member) protrudes from the protection member 10, and both the distal-end surface and the lateral surfaces of the distal portion of the knife 7 are exposed.

In a second treatment mode, the protection member 10 and the second treatment member are both outside the flexible sheath 20, and the first treatment member is activated. As in the preparation mode, the protection member 10 covers at least the distal portion of the second treatment member so that the second treatment member does not cause accidental mechanical or electrical trauma to surrounding tissue. The entire distal portion of the second treatment member, including the distal-end surface, can be fully housed within the protection member 10 as shown in FIG. 3B, or the treatment device 1 can be configured such that a distal-end surface of the knife 7 is exposed at the distal end of the protection member 10, but lateral surfaces of the knife 7 are effectively entirely covered by the protection member 10 as shown in FIG. 3A. Thus, even if the distal-end surface of the second treatment member is exposed, the protection member 10 covers enough of the second treatment member to prevent the second treatment member from mechanically or electrically impacting any surrounding tissue.

In embodiments described above, the first treatment member is a snare 6, and the second treatment member is a knife 7. However, the disclosed embodiments are not limited to this configuration. Various treatment members can be selected depending on the intended application and operator preferences.

For example, different treatment members can be selected for injection or cutting. Example treatment members are shown in FIGS. 6A-6H.

Figures 6A, 6B, 6C, 6D, 6E, 6F, 6G, 6H:
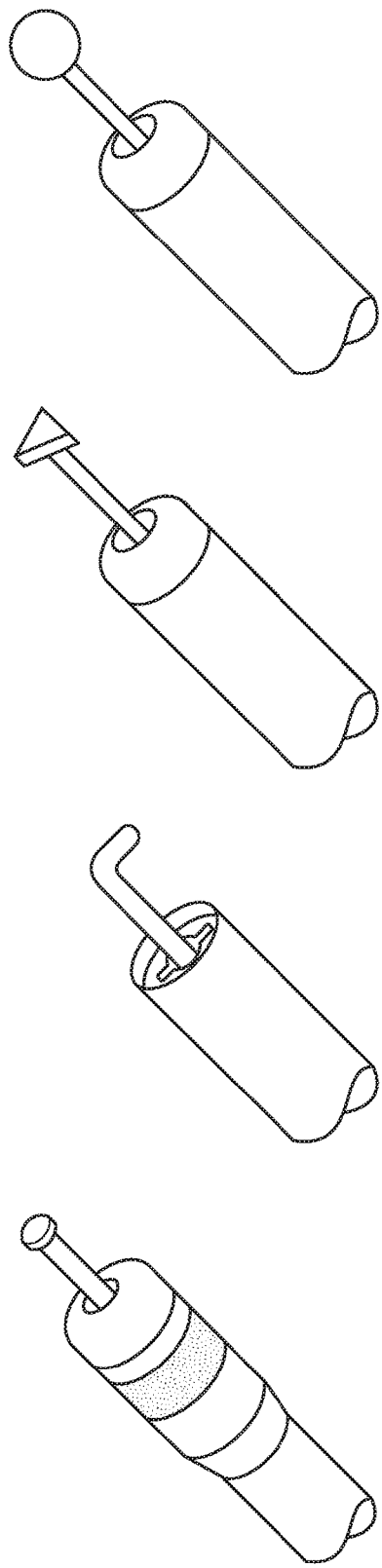
FIGS. 6A-6H show various instruments that can be used with the treatment device.

The first or second treatment member may be a diathermic knife, in which cutting is performed by applying high-frequency current. The diathermic knife may be formed of stainless steel, for example. FIGS. 6A-6C depict diathermic knives having various shapes. For example, the distal end of the knife can be blunt and/or hemispherical (FIG. 6A), hooked (FIG. 6B), or triangular (FIG. 6C). However, any shape can be used as long as the knife can pass through the lumen of the protection member 10.

The knife may optionally include an insulated tip, as shown in FIG. 6D. In this case, cutting is performed along the length of the knife and not at the tip, which is insulated from the high-frequency current. Additionally, the knife may include a dedicated port for expelling or injecting fluid at the treatment site.

The working length of the knife (the length when fully extended) can range from about 1.5 to 4.5 mm, for example. When not in use, the knife can be entirely or substantially covered by the protection member 10 and flexible sheath 20. "Substantially covered" means that only a negligible length of the knife remains exposed such that the exposed knife length is significantly smaller than the outer diameters of the protection member 10 and flexible sheath 20, and the risk of accidental tissue trauma is minimal or non-existent. For example, about 0.1 to 0.3 mm of the knife length may remain exposed in the preparation mode.

As discussed above, the first treatment member may also be a diathermic snare (FIG. 6F). The diathermic snare may be formed of stainless steel, for example. The loop section of the snare can have an approximately circular or elliptical (oval) shape, or it can have an asymmetrical crescent shape. The snare wire can be a stranded wire (comprising a plurality of elemental wires stranded together) or a monofilament wire. The dimensions of the loop section will vary depending on the intended application and operator preference; however, the loop diameter typically ranges from about 10 to 25 mm.

Other possible treatment members may be suitable for other endoscopic procedures, such as endoscopic retrograde cholangiopancreatography and sphincterotomy. These other treatment members include an injection needle (FIG. 6E) for injecting fluid at the treatment site, a needle knife (FIG. 6G) for performing pre-cutting, and an EST knife (sphincterotome) (FIG. 6H) for cutting.

Different combinations of treatment members can be used depending on the intended application and operator preferences. For example, for ESD applications, the operator might select a "dual-knife" treatment device in which the first treatment member is a knife with an insulated tip, and the second treatment member is any of the knives shown in FIGS. 6A-6C. In this case, the second treatment member knife may be an extension of the first treatment member knife, and the entire protected second treatment member can function as the insulated tip of the first treatment member knife. Or, the treatment device can instead include an injection needle (FIG. 6E) as the second treatment member.

For EMR, it might be suitable to select a treatment device in which the first treatment member is a snare (FIG. 6F) and the second treatment member is an injection needle (FIG. 6E). For endoscopic sphincterotomy (EST), the operator might use a treatment device in which the first treatment member is an EST knife (FIG. 6H) and the second treatment member is a needle knife (FIG. 6G). However, embodiments of the invention are not limited to these example combinations, and other combinations are possible.

FIGS. 7A and 7B show first and second treatment modes of the "dual-knife" treatment device in which the first treatment member is a knife with an insulated tip, and the second treatment member is the knife shown in FIG. 6A. The first treatment member knife and the second treatment member knife are extensions of a single knife 7a, and are formed integrally with each other. A protection tube 15, which can function as a second protection member, is fixed to the proximal end of the spring 11 and an outer circumference of the knife 7a. The distal end of the spring 11 is connected to an internal portion of the protection member 10. Accordingly, when the knife 7a moves in the distal direction, the protection tube 15 and the proximal end of the spring 11 will also move in the distal direction, and the spring 11 will be compressed against the protection member 10 while the protection member 10 is press fit into the flexible sheath 20.

The protection tube 15 is formed of an insulating material and has an elongated tubular body and a proximal end face that covers and protects a proximal end of the spring 11 and the portion of the knife 7a that extends within the spring 11. The knife 7a extends through an orifice in the proximal end face of the protection tube.

When the dual-knife treatment device is in the first treatment mode as shown in FIG. 7A, a distal portion of the knife 7a extends from the distal end of the protection member 10, and the remainder of the knife 7a is housed within the protection member 10 and flexible sheath 20. The protection member 10 is press fit into the flexible sheath 20.

When the dual-knife treatment device is in the second treatment mode as shown in FIG. 7B, the protection member 10 is ejected from the flexible sheath 20 and the spring 11 returns to its neutral, not compressed state. Preferably, the protection tube 15 remains housed within the protection member 10 even when the treatment device is in the second treatment mode in order to maximize the length of the knife 7a that is exposed between the protection tube 15 and flexible sheath 20.

The treatment device 1 may be part of a medical system that includes a power source (not shown), such as a radio frequency (RF) generator or an electrosurgical unit (ESU), electrically coupled to the first and second treatment members. The treatment members may be electrically coupled to the power source via the handle assembly 3, which may include a conductive member integrated within the handle assembly 3 via electrical cabling that electrically couples the handle assembly 3 with the power source.

Accordingly, the treatment members may be part of an active path that supplies electrical current to a target tissue portion of underlying tissue at a treatment site within a patient to perform an electrosurgical procedure on the target tissue portion. The power source, when activated, may deliver the electrical current to the treatment members. The treatment members may be electrically coupled to the power source in a monopolar configuration, in which a return path includes a neutral electrode positioned on the patient and electrically coupled to a return port of the power source. For other configurations, the treatment members may have a bipolar configuration with the power source, in which the return path may extend within and/or alongside the flexible sheath 20 back to the return port.

The treatment device 1 may be removably connected with the power source and/or may perform several electrosurgical procedures with different power sources. Various configurations may be possible.

As described below, the operator can manipulate the treatment device 1 between three different treatment modes in which the protection member 10 covers different portions of the second treatment member.

As discussed above, the control wire 5, first and second treatment members, energization member, and protection member 10 are all connected to each other and move together along a longitudinal axis A of the treatment device 1 (see FIGS. 2A-2B). Accordingly, the treatment device 1 can be alternated between three different modes: a preparation mode (FIG. 5A) in which the second treatment member is optionally minimally exposed or otherwise none of the treatment members are exposed, a first treatment mode (FIG. 5B) in which only the second treatment member is exposed, and a second treatment mode (FIG. 5C) in which only the first treatment member is exposed. For simplicity when referring to the drawings, the first and second treatment modes will be referred to as the knife mode and snare mode, respectively. However, the first and second treatment modes can be used with other types of treatment members.

The treatment device 1 is inserted into the patient in the preparation mode, which represents an initial state. In this mode, the two lateral rings 3a of the handle assembly 3 are positioned at a distance Di from a proximal end of the handle assembly 3, and the control wire 5 is retracted proximally into the flexible sheath 20. The spring 11, knife 7, and protection member 10 (other than the distal protruding portion 10c) are also stored in the flexible sheath 20. The proximal protruding portion 10b of the protection member 10 is press fit into the flexible sheath 20, preventing unintentional ejection of the protection member 10 from the flexible sheath 20.

In the preparation mode, the treatment members (snare 6 and knife 7) are retracted into the flexible sheath 20. Thus, even if the power source is activated (high-frequency current is delivered to the treatment members), there is minimal or no risk of accidental cutting or other trauma to the tissue when positioning the treatment device 1 because the treatment members are housed within the insulating flexible sheath 20 and covered by the protection member 10. Although a short length of the second treatment member may optionally protrude from the protection member 10 in the preparation mode, the length is sufficiently short to prevent accidental trauma. In particular, the treatment device 1 can be configured such that only a distal-end surface of the second treatment member is exposed, and the remainder of the distal portion of the second treatment member (including lateral surfaces) is effectively entirely covered by the protection member 10. Alternatively, the second treatment member may be fully housed within the flexible sheath 20 and protection member 10 in the preparation mode. In FIG. 5A, a distal-end surface of the knife 7 is shown protruding from the distal end of the protection member 10, but the exposed length of the knife 7 is sufficiently shorter than the diameter of the flexible sheath 20 such that risk of accidental trauma is adequately mitigated. In this case, the knife 7 can be used for marking or to stop bleeding, but cannot be effectively used for cutting tissue.

To switch the treatment device 1 to the knife mode, the operator applies a force FA to move the two lateral rings 3a of the handle assembly 3 in the distal direction so that the lateral rings 3a are positioned at a distance D2 from the proximal end of the handle assembly 3 (where D2>Di). The plug, which is connected to the two lateral rings 3a, advances the control wire 5, knife 7, and snare 6 in the distal direction. As the knife 7 moves distally, it projects from the flexible sheath 20. However, the snare 6 remains fully housed in the flexible sheath 20 when the treatment device 1 is in knife mode.

The proximal end of the spring 11, which is connected to the distal end of the snare 6, also moves in the distal direction when the control wire 5 is advanced in the distal direction. However, the force FA is less than required to overcome the press fit of the protection member 10, and thus the protection member 10 remains press fit into the flexible sheath 20. Thus, even though the proximal end of the spring 11 moves distally, the distal end of the spring 11 remains fixed to the unmoving protection member 10. As a result, the spring 11 is compressed, and the snare 6 remains housed within the flexible sheath 20. Accordingly, in the knife mode, the knife 7 projects from the flexible sheath 20, and the snare 6 remains housed within the flexible sheath 20.

To switch the treatment device 1 to the snare mode, the operator applies a force Fb, which is sufficient to overcome the press fit of the protection member 10, in order to move the two lateral rings 3a of the handle assembly 3 even further in the distal direction so that the lateral rings 3a are positioned at a distance D3 from the proximal end of the handle assembly 3 (where D3>D2>Di). The force FB is larger than the force FA (FB>FA). The plug, which is connected to the two lateral rings 3 a, further advances the control wire 5, knife 7, and snare 6 in the distal direction.

As the operator applies the force FB to the rings, the spring 11 is further compressed until the spring 11 reaches a state of maximum compression. At that point, the force FB is transmitted to the protection member 10 and is no longer absorbed by the spring 11. As a result of the applied force FB, the protection member 10 is ejected from the end of the flexible sheath 20, releasing the snare 6. At this point, the protection member 10 is only connected, at its proximal end, to the spring 11. Thus, once the protection member 10 is ejected from the flexible sheath 20 and the spring 11 decompresses (returns to a neutral, not compressed state), the spring 11 pushes the protection member 10 distally with respect to the knife 7 so that the protection member 10 again covers the knife 7. The snare 6 expands as it is released from the flexible sheath 20. Accordingly, in the snare mode, both the knife 7 and the snare 6 are projected from the flexible sheath 20, but the knife 7 is covered by the protection member 10.

The operator can also switch the treatment device 1 from the snare mode to the knife mode and from the knife mode to the preparation mode as needed by pulling the two rings in the proximal direction with the appropriate amount of force (not shown). To switch from the snare mode to the knife mode, the operator must pull with enough force to overcome the resistance between the proximal protruding portion 10b of the protection member 10 and the distal end of the flexible sheath 20 so that the distal end of the protection member 10 is again press fit into the flexible sheath 20. To switch from the knife mode to the preparation mode, the operator need only pull with an amount of force sufficient to retract the knife back into the flexible sheath 20.

The following describes an example method of performing a tissue resection operation using a treatment device according to the disclosed embodiments. The tissue resection operation may be performed to remove a target tissue portion at a treatment site within a patient. The target tissue portion may be a polyp, for example. Description of the method is made with reference to FIGS. 8A-8E.

Figure 8A:
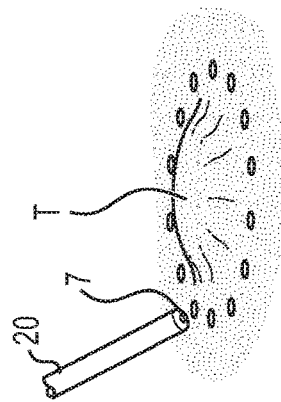
FIGS. 8A-8E show a method of performing a hybrid ESD procedure using a treatment device of the disclosed embodiments.

The operator can position the treatment device 1 within the patient (via an endoscope) while the treatment device 1 is in the preparation mode. The power source may be activated while the treatment device 1 is in the preparation mode, or may be activated later. Even if the power source is activated while the treatment device 1 is still in the preparation mode, the lateral surfaces of the knife 7 will be protected by the flexible sheath 20 and protection member 10. While in the preparation mode, the operator can mark the perimeter of the target tissue portion T using the distal end of the knife (FIG. 8A).

Figure 8B:
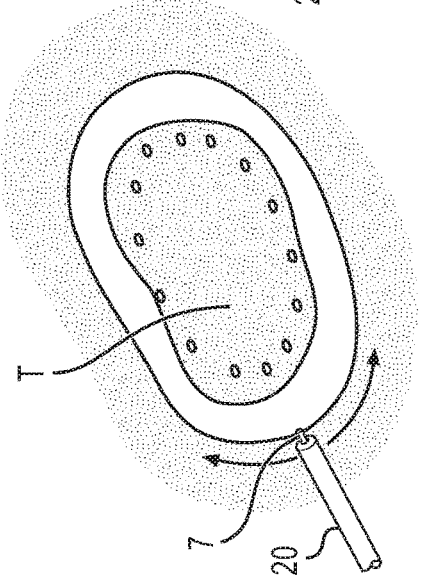

After marking is completed, the operator can switch the treatment device 1 to knife mode by pushing the lateral rings 3a with a force FA SO that the lateral rings 3a are positioned at a distance D2 from the proximal end of the handle assembly 3. FIGS. 8 A and 8B show the distal portion of the flexible sheath 20 when the treatment device 1 is in the knife mode. The knife 7 is shown projecting from the distal end of the flexible sheath 20. The power source is activated at this time if it has not already been activated. Using the treatment device 1 in knife mode, the operator cuts around the perimeter of the target tissue portion T in order to isolate the target tissue portion T from the surrounding tissue (FIG. 8B). The electrical current stops any active bleeding. If the knife also has the capacity to inject fluid, then saline can be injected around the perimeter of the target tissue portion T in order to elevate the target tissue portion T from the surrounding tissue before cutting (not shown).

Figure 8C:
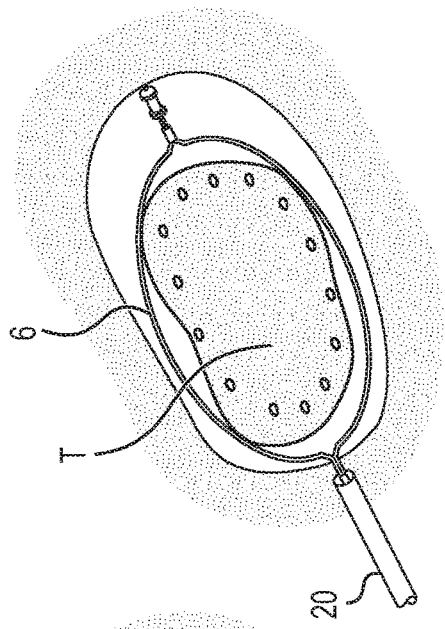
Figure 8D:
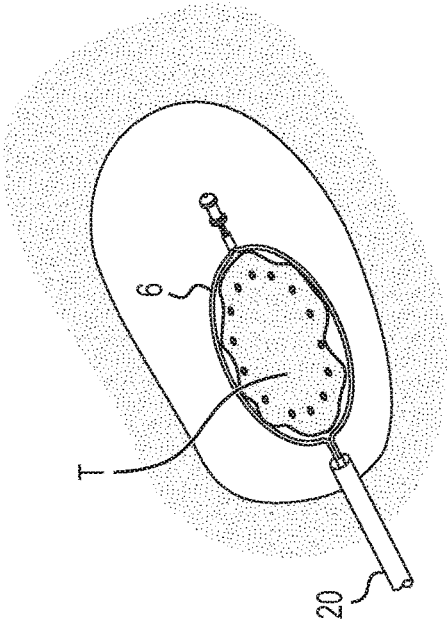

The operator can then switch the treatment device 1 to snare mode by further pushing the lateral rings 3a with a force FB so that the lateral rings 3a are positioned at a distance D3 from the proximal end of the handle assembly 3. FIG. 8C shows the distal portion of the flexible sheath 20 when the treatment device 1 is in the snare mode. The loop section 6a of the snare 6 is positioned around the isolated target tissue portion T. After positioning the distal loop in a desired position around the base of the isolated target tissue portion T, electrical current is applied via the snare 6 to the base portion as the snare 6 is retracted in order to collapse the snare 6 and finish resecting the target tissue portion T (see FIG. 8D).

Figure 8E:
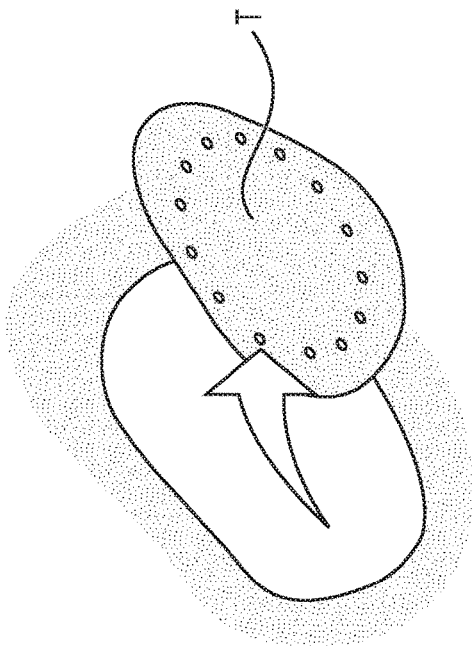

Finally, the resected target tissue portion T is removed as shown in FIG. 8E.

The illustrated exemplary embodiments of the diathermic endotherapeutic device and system as set forth above are intended to be illustrative and not limiting and can be combined. Various changes may be made without departing from the spirit and scope of the invention.

What is claimed is:

1. A treatment device comprising:
a flexible sheath;
a wire configured to be inserted into the sheath;
a first treatment member disposed at distal side from the wire;
a second treatment member disposed at a distal side from the first treatment member; and
a protection member configured to cover the second treatment member when the first treatment member projects from a distal end of the sheath.

2. The treatment device according to claim 1, wherein
when the treatment device is in a first treatment mode, the second treatment member projects from a distal end of the protection member, and
when the treatment device is in a second treatment mode, the first treatment member projects from the distal end of the sheath, and the protection member covers the second treatment member.

3. The treatment device according to claim 2, wherein the treatment device is configured to switch between the first and second treatment modes in response to axial movement of the wire.

4. The treatment device according to claim 2, wherein when the treatment device is in a preparation mode, the first treatment member is disposed within the sheath, and the second treatment member is substantially covered by the protection member and the sheath.

5. The treatment device according to claim 2, further comprising:
an energization member connected to a proximal end of the protection member and configured to energize the protection member in a distal direction so that the protection member covers the second treatment member.

6. The treatment device according to claim 2, wherein:
the protection member comprises a distal protruding portion at a distal end of the protection member, and an outer diameter of the distal protruding portion decreases in an axial direction from a center region of the distal protruding portion toward each of a proximal end and a distal end of the distal protruding portion.

7. The treatment device according to claim 2, wherein a proximal end of the protection member is configured to be press fit into the distal end of the sheath.

8. The treatment device according to claim 7, further comprising:
a metal member disposed around an outer circumference of a distal portion of the sheath and configured to control radial expansion of the distal portion of the sheath when the protection member is press fit into the distal end of the sheath.

9. The treatment device according to claim 7, wherein the protection member comprises:
an elongated tubular section that extends in a longitudinal direction of the treatment device; and
an elastic member disposed around an outer circumference of at least a portion of the elongated tubular section, and
the elastic member is configured to contact an inner surface of the sheath when the protection member is press fit into the distal end of the sheath.

10. The treatment device according to claim 9, further comprising:
a metal member disposed around an outer circumference of a distal portion of the sheath and configured to control radial expansion of the distal portion of the sheath when the protection member is press fit into the distal end of the sheath.

11. The treatment device according to claim 9, wherein:
a distal end of the energization member is connected to the proximal end of the protection member, and a proximal end of the energization member is connected to at least one of the first and second treatment members.

12. The treatment device according to claim 11, wherein:
the energization member is a spring, and
in the first treatment mode, the proximal end of the protection member is press fit into the distal end of the sheath and the spring is compressed, and
in the second treatment mode, the protection member is detached from the sheath and the spring is not compressed.

13. The treatment device according to claim 2, wherein:
when the treatment device is in the second treatment mode, the protection member covers a distal portion of the second treatment member.

14. The treatment device according to claim 13, wherein:
when the treatment device is in the second treatment mode, lateral surfaces of the second treatment member are covered by the protection member.

15. The treatment device according to claim 14, wherein:
when the treatment device is in the second treatment mode, a distal-end surface of the second treatment member is covered by the protection member.

16. A treatment device comprising:
a flexible sheath;
a wire configured to move axially within the sheath;
a snare connected to a distal end of the wire;
a knife connected to a distal end of the snare; and
a protection member configured to cover the knife.

17. The treatment device according to claim 16, further comprising:
a spring having a distal end that is connected to a proximal end of the protection member, and having a proximal end that is connected to at least one of the snare and the knife, the spring being configured to energize the protection member in a distal direction so that the protection member covers the knife,
wherein:
when the treatment device is in a first treatment mode, the knife projects from a distal end of the protection member, and
when the treatment device is in a second treatment mode, the snare projects from a distal end of the sheath, and the protection member covers the knife.

18. The treatment device according to claim 17, wherein:
in the first treatment mode, the proximal end of the protection member is press fit into the distal end of the sheath and the spring is compressed, and
in the second treatment mode, the protection member is detached from the sheath and the spring is not compressed.

19. The treatment device according to claim 17, further comprising:
a connection tube covering a junction between the distal end of the snare and a proximal end of the knife.

20. The treatment device according to claim 19, further comprising:
a cylindrical spacer disposed between the knife and the connection tube.

* * * * *